(12) United States Patent
Zu et al.

(10) Patent No.: US 11,021,743 B2
(45) Date of Patent: Jun. 1, 2021

(54) DETERMINATION OF NUCLEIC ACID METHYLATION

(71) Applicant: Agency for Science, Technology and Research, Singapore (SG)

(72) Inventors: Yanbing Zu, Singapore (SG); Jackie Y. Ying, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 142 days.

(21) Appl. No.: 15/778,876

(22) PCT Filed: Nov. 25, 2016

(86) PCT No.: PCT/SG2016/050583
§ 371 (c)(1),
(2) Date: May 24, 2018

(87) PCT Pub. No.: WO2017/091156
PCT Pub. Date: Jun. 1, 2017

(65) Prior Publication Data
US 2019/0017110 A1    Jan. 17, 2019

(30) Foreign Application Priority Data
Nov. 27, 2015    (SG) .............................. 10201509792S (51) Int. Cl.
C12Q 1/68        (2018.01)
C12Q 1/6858      (2018.01)
C12Q 1/6886      (2018.01)

(52) U.S. Cl.
CPC ......... *C12Q 1/6858* (2013.01); *C12Q 1/6886* (2013.01); *C12Q 2523/125* (2013.01); *C12Q 2525/113* (2013.01); *C12Q 2535/131* (2013.01); *C12Q 2537/163* (2013.01); *C12Q 2563/155* (2013.01); *C12Q 2565/107* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 5,472,881 A | 12/1995 | Beebe et al. | |
| 8,623,599 B2* | 1/2014 | Devos ................... | C12Q 1/6806 435/6.1 |
| 2008/0241828 A1* | 10/2008 | Wu ....................... | C12Q 1/6827 435/6.14 |

FOREIGN PATENT DOCUMENTS

| | | | |
|---|---|---|---|
| CN | 102884204 A | 1/2013 | |
| CN | 103789429 A | 5/2014 | |
| CN | 105026580 A | 11/2015 | |
| EP | 2189538 A1 | 5/2010 | |
| WO | 03048769 A1 | 6/2003 | |
| WO | 2011087456 A1 | 7/2011 | |
| WO | 2014168582 A1 | 10/2014 | |
| WO | 2015041603 A1 | 3/2015 | |

OTHER PUBLICATIONS

Cottrell et al. (Nucleic Acids Research, 2004, vol. 32, No. 1, e10, p. 1-8) (Year: 2004).*
Wu et al. (Analytical Chemistry, 2013, vol. 85, p. 4376-4383) (Year: 2013).*
Shin et al. (Sensors and Actuators B, 2013, 177, p. 404-411) (Year: 2013).*
International Preliminary Report on Patentability for International Application No. PCT/SG2016/050583 dated May 29, 2018, pp. 1-7.
Flanagan et al., "A Cystosine Analog That Confers Enhanced Potency to Antisense Oligonucleotides," Proc. Natl. Acad. Sci., vol. 96, No. 7, Mar. 30, 1999, pp. 3513-3518.
Kumar et al., "The First Analogues of LNA (Locked Nucleic Acids): Phosphorothioate-LNA and 2'-thio-LNA," Bioorg. Med. Chem. Lett., vol. 8, No. 9, Aug. 18, 1998, pp. 2219-2222.
Wahlestedt et al., "Potent and Nontoxic Antisense Oligonucleotides Containing Locked Nucleic Acids," Proc. Natl. Acad. Sci., vol. 97, No. 10, May 9, 2000, pp. 5633-5638.
Mucic et al., Synthesis and Characterization of DNA with Ferrocenyl Groups Attached to Their 5'-Termini: Electrochemical Characterization of a Redox-Active Nucleotide Monolayer, Chemical Communications, vol. 4, 1196, pp. 555-557.
Grabar et al., "Preparation and Characterization of Au Colloid Monolayers," Anal. Chem., vol. 67, 1995, pp. 735-743.
Zu et al. "Sequence-Selective Recognition of Nucleic Acids under Extremely Low Salt Conditions Using Nanoparticle Probes," Anal. Chem., vol. 83, No. 11, Jun. 1, 2011, pp. 4090-4094.
Zu, et al. "Visualizing Low-Level Point Mutations: Enzyme-like Selectivity Offered by Nanoparticle Probes," Small, vol. 7, No. 3, Feb. 7, 2011, pp. 306-310.
Cottrell, et al., "A Real-Time PCR Assay for DNA-Methylation Using Methylation-Specific Blockers," Nucleic Acids Res, vol. 32, No. 1, Jan. 13, 2004, pp. e10: 1-8.
Zu, et al., "Nanoprobe-Based Genetic Testing," Nanotoday, vol. 9 No. 2, Apr. 2014, pp. 166-171.

(Continued)

Primary Examiner — Stephanie K Mummert
(74) Attorney, Agent, or Firm — Winstead PC (57) ABSTRACT

The invention relates to methods and kits for determining the methylation status of a target nucleic acid molecule in a sample comprising (a) bisulfite treatment of the target nucleic acid, (b) amplifying the treated target nucleic acid with methylation-specific primers, (c) contacting the amplicons with a methylation-specific plasmonic nanoprobe and (d) determining the methylation status based on melting temperature $T_m$ of the hybrid probe and the target nucleic acid. In particular, a plasmonic gold nanoparticle covalently coupled to a morpholino oligonucleotide probe. Also claimed are methods and kits for determining methylation status of the Septin 9 (SEPT9) gene promoter.

5 Claims, 3 Drawing Sheets
Specification includes a Sequence Listing.

(56) References Cited

OTHER PUBLICATIONS

Danese, et al., "Comparison of Genetic and Epigenetic Alterations of Primary Tumors and Matched Plasma Samples in Patients with Colorectal Cancer," PLoS One, vol. 10, No. 5, May 6, 2015, pp. e0123417: 1-11.

Barekati, et al., "Specificity of Methylation Assays in Cancer Research: A Guidelines for Designing Primers and Probes," Obstetrics and Gynecology International, vol. 2010, Jul. 27, 2010, pp. 870865:1-7.

Written Opinion of the International Searching Authority for International Application No. PCT/SG2016/050583 dated Feb. 15, 2017, pp. 1-6.

Office Action for Chinese Patent Application No. 201680079795.7 dated Mar. 10, 2021, pp. 1-8.

Sina et al., "eMethylsorb: Electrochemical Quantification of DNA Methylation at CpG Resolution Using DNA-Gold Affinity Interactions," Chemical Communications, vol. 50, No. 86, Sep. 2014, pp. 1-4.

Warren et al., "Septin 9 Methylated DNA is a Sensitive and Specific Blood Test for Colorectal Cancer," BMC Medicine, vol. 9, No. 133, 2011, pp. 1-9.

* cited by examiner

| Sample | NTC | Negative Control | SW480 | RKO | LS174T |
|---|---|---|---|---|---|
| Result | | | | | |

*NTC = no-template control

DETERMINATION OF NUCLEIC ACID METHYLATION

This application makes reference to and claims the benefit of priority of the Singapore Patent Application No. 10201509792S filed on Nov. 27, 2015, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to methods and kits for detection of DNA methylation.

BACKGROUND OF THE INVENTION

Epigenetic modifications of human genes are emerging as promising biomarkers for early diagnosis of cancer. In particular, DNA methylation of the promoter regions of cancer suppression genes is usually associated with aberrant gene regulation involved in the predisposition, initiation, and progression of cancer. Therefore, the DNA methylation biomarkers could be ideal targets for the early detection of cancer and for the monitoring of cancer progression.

For example, recent studies showed that blood-based detection of Septin 9 (SEPT9) gene methylation may be used as a non-invasive method for colorectal cancer screening. The circulating cell-free DNA (cfDNA) fragments released from tumor cells allow for early detection of the aberrant DNA alteration. It has been reported that the clinical sensitivity and specificity of the SEPT9 test could be higher than 70%. Compared to the colonoscopic-based surveillance, the DNA assay is much more convenient and should improve patient compliance to the screening. However, to gauge the epigenetic change of the rare circulating tumor cfDNA in a large background of normal DNA is very challenging. Highly sensitive and specific detection is required.

Various technologies have been existing in the prior art for the determination of nucleic acid methylation. However, there still remains a considerable need for new technologies to overcome the drawbacks of existing technologies.

SUMMARY OF THE INVENTION

The present invention satisfies the aforementioned need in the art by providing a new method for determing nucleic acid methylation.

In one aspect, the present invention provides a method of determining the methylation status of a target nucleic acid molecule in a sample, wherein the method comprises the steps of:
(a) bisulfite treatment of the sample for converting the unmethylated cytosine bases in the target nucleic acid molecule to uracil;
(b) amplifying at least part of the converted target nucleic acid molecule, said part comprising a target region the methylation status of which is to be analyzed, in a polymerase chain reaction (PCR), using a pair of methylation-specific primers under conditions allowing such amplification to generate PCR amplification products (amplicons);
(c) contacting the amplicons with a methylation-specific plasmonic nanoprobe comprising a plasmonic nanoparticle and a non-ionic oligonucleotide analog probe covalently coupled thereto, the oligonucleotide analog probe comprising a base sequence that is complementary to the target region, under conditions that allow the oligonucleotide analog probe and the amplicons comprising the target region to hybridize to each other, wherein the probe generates a detectable signal if hybridized to the target nucleic acid molecule that is distinguishable from the signal of the unhybridized probe;
(d) determining the methylation status of the target nucleic acid molecule based on the determination of the melting temperature $T_m$ of the hybrid of the nanoprobe and the target nucleic acid.

In various embodiments, the methylation status of one or more CpG islands within the target nucleic acid molecule is determined.

In various embodiments, asymmetric PCR (aPCR) is used in step (b) of the method disclosed herein.

In various embodiments, at least one of the methylation-specific primers hybridizes to the converted target nucleic acid molecule at a region comprising one or more CpG islands, such that the primer pair preferably hybridizes to the converted methylated nucleic acid molecule over the converted unmethylated molecule during the PCR.

In various embodiments, a blocker sequence is added during the PCR to minimize the amplification of the converted unmethylated nucleic acid molecule.

In various embodiments, the plasmonic nanoparticle used in step (c) of the method disclosed herein is a plasmonic gold nanoparticle.

In various embodiments, the non-ionic oligonucleotide analog probe used in step (c) of the method disclosed herein is a morpholino oligonucleotide probe.

In various embodiments, the detectable signal in step (c) of the method disclosed herein is the color of the assay solution that is indicative of whether the probe is hybridized to the amplicons or not.

In various embodiments, the melting temperature in step (d) of the method disclosed herein is indicated by a color change caused by nanoprobe dissociation and subsequent aggregation.

In various embodiments, the method disclosed herein further comprises isolating genomic DNA from the sample prior to step (a).

In various embodiments, the method further comprises using a nucleic acid molecule comprising the unmethylated target nucleotide sequence as a negative control, and/or using a nucleic acid molecule comprising the methylated target nucleotide sequence as a positive control.

In various embodiments, the target nucleic acid molecule is the human Septin 9 (SEPT9) gene promoter, the methylation-specific primers have the nucleic acid sequences 5'-ATTAGTTATTATGTCGGATTTCGC-3' (SEQ ID NO: 1) and 5'-CAACACGTCCGCGACCG-3' (SEQ ID NO: 2), the blocker has the nucleic acid sequence 5'-GTTATTATGTTG-GATTTTGTGGTTAATGTGTAG-3' and is labelled with C3 spacer at the 3' end (SEQ ID NO: 3), and the oligonucleotide analog probe used is a morpholino oligonucleotide having the nucleic acid sequence 5'-CAACTACGCGTTAACCGC-GATTTTT -3' (SEQ ID NO: 4).

In various embodiments, the method is used to determine the methylation status of the human Septin 9 (SEPT9) gene promoter, preferably in the cell-free DNA (cfDNA) fragments circulating in the blood released from colorectal cancer cells.

In another aspect, the invention provides a kit for determining the methylation status of a target nucleic acid molecule in a sample, preferably of one or more CpG islands within said target nucleic acid molecule, wherein the kit comprises a pair of methylation-specific primers and a methylation-specific plasmonic nanoprobe for use in a method disclosed herein.

In various embodiments, the kit further comprises a blocker sequence for use in the method disclosed herein.

In various embodiments, the kit further comprises bisulfite or a salt thereof.

In various embodiments, the target nucleic acid molecule is the human SEPT9 gene promoter, and the kit comprises a pair of methylation-specific primers having the nucleic acid sequences 5'-ATTAGTTATTATGTCGGATTTCGC-3' (SEQ ID NO: 1) and 5'-CAACACGTCCGCGACCG-3' (SEQ ID NO: 2), and a plasmonic gold nanoparticle functionalized with a morpholino oligonucleotide having the nucleic acid sequence 5'-CAACTACGCGTTAACCGCGATTTTT-3' (SEQ ID NO: 4).

In various embodiments, the kit further comprises a blocker having the nucleic acid sequence 5'-GTTAT-TATGTTGGATTTTGTGGTTAATGTGTAG-3' and is labelled with C3 spacer at the 3' end (SEQ ID NO: 3).

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

The object of the present invention is to provide a method of determining the methylation status of a target nucleic acid molecule in a sample.

To this end, the inventors of the present invention have provided such a method employing methylation-specific polymerase chain reaction (PCR) and plasmonic nanoprobe-based detection.

In one aspect, disclosed herein is a method of determining the methylation status of a target nucleic acid molecule in a sample, preferably of one or more CpG islands within said target nucleic acid molecule, wherein the method comprises the steps of:

(a) bisulfite treatment of the sample for converting the unmethylated cytosine bases in the target nucleic acid molecule to uracil;

(b) amplifying at least part of the converted target nucleic acid molecule, said part comprising a target region the methylation status of which is to be analyzed, in a polymerase chain reaction (PCR), preferably asymmetric PCR (aPCR), using a pair of methylation-specific primers under conditions allowing such amplification to generate PCR amplification products (amplicons);

(c) contacting the amplicons with a methylation-specific plasmonic nanoprobe comprising a plasmonic nanoparticle, preferably a plasmonic gold nanoparticle, and a non-ionic oligonucleotide analog, preferably morpholino oligonucleotide (MOR), probe covalently coupled thereto, the oligonucleotide analog probe comprising a base sequence that is complementary to the target region, under conditions that allow the oligonucleotide analog probe and the amplicons comprising the target region to hybridize to each other, wherein the probe generates a detectable signal if hybridized to the target nucleic acid molecule that is distinguishable from the signal of the unhybridized probe, wherein said detectable signal is preferably the color of the assay solution that is indicative of whether the probe is hybridized to the amplicons or not;

(d) determining the methylation status of the target nucleic acid molecule based on the determination of the melting temperature $T_m$ of the hybrid of the nanoprobe and the target nucleic acid, wherein the melting temperature is preferably indicated by a color change caused by nanoprobe dissociation and subsequent aggregation.

In certain embodiments, the method disclosed herein may further comprise isolating genomic DNA from the sample prior to step (a).

The presently described method is used to determine the methylation status (i.e., the location and/or degree of methylation) of one or more cytosines of the target nucleic acid molecule in a sample. In some embodiments, the differences in the base composition of the target nucleic acid molecule relative to the canonical unmethylated sequence thereof is used to determine the extent of methylation.

In preferred embodiments, the methylation status of one or more CpG islands within the target nucleic acid molecule is determined. CpG islands are regions of the genome containing clusters of CpG dinucleotides. These clusters frequently appear in the 5' ends of genes. Methylation of CpG islands is known to play a role in transcriptional silencing in higher organisms. The cytosine bases of most CpG dinucleotides in the human genome are methylated, but the cytosine bases in CpG islands are usually unmethylated.

The terms "nucleic acid molecule", "nucleic acid sequence" or "oligonucleotide", as used herein, relate to any nucleic acid molecule in any possible configuration, including single-stranded, double-stranded configurations or a combination thereof.

The term "sample" as used herein refers to anything capable of being analyzed by the methods described herein. In some embodiments, the sample comprises or is suspected to comprise one or more nucleic acids capable of analysis by the methods. In certain embodiments, for example, the samples comprise nucleic acids (e.g., DNA, RNA, cDNAs, etc.). Samples can include, for example, cells, blood, semen, saliva, urine, feces, rectal swabs, and the like. In some embodiments, the samples are "mixture" samples, which comprise nucleic acids from more than one subject or individual. In some embodiments, the methods provided herein comprise purifying the sample or purifying the nucleic acid(s) from the sample. In some embodiments, the sample is purified nucleic acid.

The term "bisulfite treatment" as used herein refers to the treatment of a sample with bisulfite or a salt thereof (e.g. sodium bisulfate) for subsequent methylation analysis. Treatment of nucleic acid molecules (e.g. DNA) with bisulfite converts unmethylated cytosine residues to uracil, but leaves 5-methylcytosine residues unmodified. Thus, bisulfite treatment introduces specific changes in the nucleic acid base composition that depend on the methylation status of individual cytosine residues. In some embodiments, bisulfate treatment yields single-nucleotide resolution information about the methylation status of a segment of DNA.

Following bisulfate treatment, at least part of the converted target nucleic acid molecule is amplified by PCR. Any PCR that may produce single-stranded amplicons for hybridization to the oligonucleotide analog probe of the methylation-specific plasmonic nanoprobe may be used in the present method. Such types of PCR technology include, but are not limited to allele-specific PCR, assembly PCR, asymmetric PCR, dial-out PCR, digital PCR, helicase-dependent amplification, hot start PCR, intersequence-specific PCR (ISSR), inverse PCR, ligation-mediated PCR, methylation-specific PCR (MSP), miniprimer PCR, multiplex ligation-dependent probe amplification (MLPA), multiplex-PCR, nanoparticle-assisted PCR (nanoPCR), nested PCR, overlap-extension PCR or splicing by overlap extension (SOEing), PAN-AC, reverse transcription PCR (RT-PCR), solid phase PCR, thermal asymmetric interlaced PCR (TAIL-PCR), touchdown PCR (step-down PCR), universal fast walking or transcription-mediated amplification (TMA). Such techniques are well-known in the art (McPherson, M J and Moller, S G (2000) PCR (Basics), Springer-Verlag Telos; first edition).

In preferred embodiments, asymmetric PCR (aPCR) is used. aPCR is a PCR wherein the amounts of the two primers are unequal. The primer present at a higher amount is referred to as the excess primer, and the strand resulting from the extension of the excess primer is accumulated in excess and is hybridized subsequently to the oligonucleotide analog probe of the methylation-specific plasmonic nanoprobe.

The methylation-specific primers are designed to specifically amplify the converted methylated target nucleic acid molecule. In certain embodiments, at least one of the methylation-specific primers hybridizes to the converted target nucleic acid molecule at a region comprising one or more CpG islands, such that the primer pair preferably hybridizes to the converted methylated nucleic acid molecule over the converted unmethylated molecule during the PCR.

In certain embodiments, a blocker sequence is added during the PCR to minimize the amplification of the converted unmethylated nucleic acid molecule.

The "blocker sequence" as used herein refers to a polynucleotide, which is usually a synthetic polynucleotide that is single-stranded and comprises a sequence that is hybridizable, and preferably complementary, to a segment of the target nucleic acid molecule, wherein the blocker sequence anneals to the target nucleic acid molecule so as to block further primer extension of the 3'-end of the first-strand cDNA at a desired position. Some embodiments of strand displacement methods of the present invention for obtaining a single-stranded DNA target sequence comprise use of a blocker sequence. The blocker sequence comprises nucleotides that bind to the target nucleic acid with an affinity, preferably a high affinity, such that the blocker sequence resists displacement by DNA polymerase in the course of primer extension, in preferably more than about 30%, more preferably more than about 50%, even more preferably more than about 75%, and most preferably more than about 90%, of primer extension events. The length and composition of the blocker sequence should be such that excessive random non-specific hybridization is avoided under the conditions of the methods of the present invention. The length of the blocker polynucleotide is preferably from about 3 to about 100 nucleotides, more preferably from about 5 to about 80 nucleotides, even more preferably from about 8 to about 40 nucleotides, and most preferably from about 10 to about 15 nucleotides. It is understood that the length can be greater or less as appropriate under the reaction conditions of the methods of this invention. The complementarity of the blocker polynucleotide is preferably at least about 25%, more preferably at least about 50%, even more preferably at least about 75%, and most preferably at least about 90%, to its intended binding sequence on the target nucleic acid. In some embodiments, the blocker sequence that hybridizes to a DNA target nucleic acid is attached to the DNA such that displacement of the blocker sequence by the polymerase that affects primer extension is substantially, or at least sufficiently, inhibited. Suitable methods for achieving such attachment include, without limitation, techniques known in the art, such as using a cytosine analog that contains a G-clamp heterocycle modification as described by Flanagan et al., (Proc. Natl. Acad. Sci. USA 96:3513-3518, 1999); and locked nucleic acids as described, e.g., by Kumar et al., (Bioorg. Med. Chem. Lett. 8:2219-2222, 1998; and by Wahlestedt et al. (Proc. Natl. Acad. Sci. USA 97:5633-5638, 2000), all of which are incorporated herein by reference. Other suitable methods include using, where appropriate, sequences with a high GC content and/or cross-linking. Any of these methods for obtaining enhanced attachment may be used alone or in combination. Alternatively, a molecule comprising a peptide nucleic acid ("PNA") can be used. Blocker sequences are optional in the methods of the present invention.

The PCR amplicons are further contacted with a methylation-specific plasmonic nanoprobe comprising a plasmonic nanoparticle and a non-ionic oligonucleotide analog probe covalently coupled thereto, the oligonucleotide analog probe comprising a base sequence that is complementary to the target region, under conditions that allow the oligonucleotide analog probe and the amplicons comprising the target region to hybridize to each other.

Without wishing to be bound to any particular theory, the probe in accordance with the present invention generates a detectable signal if hybridized to the target nucleic acid molecule that is distinguishable from the signal of the unhybridized probe. Said signal may be any signal that is detectable by any means.

In preferred embodiments, these probes indicate the presence or absence of the target by showing a color (e.g. red) in their hybridized state and another color (e.g. light grey) in their unhybridized, aggregated state. The aggregation of the unhybridized nanoprobes may generally be achieved by control of the ionic strength of the assay solution, for example by control of salt concentrations. This particular behavior of the nanoprobes, i.e. remaining in non-aggregated form as long as they are hybridized to their target and aggregated if not hybridized to their target, can be attributed to the non-ionic character of the nanoprobes.

The hybridization of the methylation-specific plasmonic nanoprobe and the amplicons in step c) of the method may be carried out at a temperature below the melting temperature of the duplex of the nanoprobe and the amplicons of the target nucleic acid molecule having the desired methylation status, i.e. typically the converted methylated nucleic acid molecule, and above that of the duplex of the nanoprobe and the amplicons of the target nucleic acid having not the desired methylation status, i.e. typically the converted unmethylated nucleic acid molecule, to allow maximum distinction between these two groups. In these embodiments, step d) may also be carried out at the above-described temperature by simply determining the color of the assay solution that is indicative of whether the hybrid has been formed or not. In these embodiments, the melting temperature of the hybrid is thus only determined insofar as it is determined whether the formed hybrid has a melting temperature above the assay temperature, indicating the presence of the target nucleic acid with the methylation status of interest, or a melting temperature below the assay temperature, indicating the absence of the target nucleic acid with the methylation status of interest.

The term "nanoparticle" as used herein refers to any particle having a size from about 1 to about 250 nm and has the capacity to be covalently coupled to at least one oligonucleotide analog as described herein. In certain embodiments, the nanoparticle is a metal nanoparticle. In other embodiments, the nanoparticle is a colloidal metal.

In some embodiments, the metal is a noble metal. Non-limiting examples of a noble metal that can be used can include silver, gold, platinum, palladium, ruthenium, osmium, iridium or mixtures thereof, not to mention a few. Other metals that can also be used in the formation of the nanoparticle can include but are not limited to aluminium, copper, cobalt, indium, nickel, or any other metal amenable to nanoparticle formation). The nanoparticle as described herein can also comprise a semiconductor (including for example and without limitation, CdSe, CdS, and CdS or CdSe coated with ZnS) or magnetic (for example, ferromagnetite) colloidal materials. Other nanoparticles useful in the practice of the invention include, also without limitation, ZnS, ZnO, Ti, $TiO_2$, Sn, $SnO_2$, Si, $SiO_2$, Fe, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs.

The size of the nanoparticle used in the conjugate of the present invention can vary in any size when desired, as long as the nanoparticle is capable of providing optical properties; for example, generate optical signals sensitive to hybridization reactions. The diameter of the nanoparticle as described herein can range in the size from about 1 nm to about 250 nm; about 1 nm to about 200 nm; about 1 nm to about 160 nm; about 1 nm to about 140 nm; about 1 nm to about 120 nm; about 1 nm to about 80 nm; about 1 nm to about 60 nm; about 1 nm to about 50 nm; about 5 nm to about 250 nm; about 8 nm to about 250 nm; about 10 nm to about 250 nm; about 20 nm to about 250 nm; about 30 nm to about 250 nm; about 40 nm to about 250 nm; about 85 nm to about 250 nm; about 100 nm to about 250 nm; or about 150 nm to about 250 nm. In some embodiments, the diameter of the diameter of the nanoparticle is in the range of about 1 nm to about 100 nm.

In certain embodiments, the nanoparticle comprises a surfactant. As used herein, "surfactant" refers to a surface active agent which has both hydrophilic and hydrophobic parts in the molecule. The surfactant can for example be used to stabilize the nanoparticles. The surfactant can also be used to prevent non-specific adsorption of the oligonucleotide analog on the surface of the nanoparticles. In some embodiments, the surfactant is a non-ionic surfactant. Other types of surfactants that can be used can include but are not limited to cationic, anionic, or zwitterionic surfactants. A particular surfactant may be used alone or in combination with other surfactants. One class of surfactants comprises a hydrophilic head group and a hydrophobic tail. Hydrophilic head groups associated with anionic surfactants include carboxylate, sulfonate, sulfate, phosphate, and phosphonate. Hydrophilic head groups associated with cationic surfactants include quaternary amine, sulfonium, and phosphonium. Quaternary amines include quaternary ammonium, pyridinium, bipyridinium, and imidazolium. Hydrophilic head groups associated with non-ionic surfactants include alcohol and amide. Hydrophilic head groups associated with zwitterionic surfactants include betaine. The hydrophobic tail typically comprises a hydrocarbon chain. The hydrocarbon chain typically comprises between about six and about 24 carbon atoms, more typically between about eight to about 16 carbon atoms.

The plasmonic nanoparticle for use in the present method is functionalized with a non-ionic oligonucleotide analog probe that preferably recognizes the amplicons of the converted methylated nucleic acid molecule over those of the converted unmethylated nucleic acid molecule. In certain embodiments, the oligonucleotide analog probe is complementary to the amplicons at a region comprising one or more CpG islands, and thus specifically recognizes the amplicons of the converted methylated nucleic acid molecule over those of the converted unmethylated molecule.

In some embodiments, the non-ionic oligonucleotide analog probe used in the presently disclosed method is a morpholino oligonucleotide probe or a derivative thereof. The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). The analogs can for example, include those having a substantially uncharged, phosphorus containing backbone.

A substantially uncharged, phosphorus containing backbone in an oligonucleotide analog can for example be one in which a majority of the subunit linkages, e.g., between 60-100%, are uncharged at physiological pH, and contain a single phosphorous atom. The oligonucleotide analog can comprise a nucleotide sequence complementary to a target nucleic acid sequence as defined below. In preferred embodiments, the oligonucleotide analogs of the present invention are phosphorodiamidate morpholino oligos, wherein the sugar and phosphate backbone is replaced by morpholine groups linked by phosphoramidates and the nucleobases, such as cytosine, guanine, adenine, thymine and uracil, are coupled to the morpholine ring or derivatives thereof.

As used herein, the term "complementary" or "complementarity" relates to the relationship of nucleotides/bases on two different strands of DNA or RNA, or the relationship of nucleotides/bases of the nucleotide sequence of the oligonucleotide analog probe and a DNA/RNA strand, where the bases are paired (for example by Watson-Crick base pairing: guanine with cytosine, adenine with thymine (DNA) or uracil (RNA)). Therefore, the oligonucleotide analog probe as described herein can comprise a nucleotide sequence that can form hydrogen bond(s) with another nucleotide sequence, for example a DNA or RNA sequence, by either conventional Watson-Crick base pairing or other non-traditional types of pairing such as Hoogsteen or reversed Hoogsteen hydrogen bonding between complementary nucleosides or nucleotides. In this context, the term "hybridize" or "hybridization" refers to an interaction between two different strands of DNA or RNA or between nucleotides/bases of the nucleotide sequence of the oligonucleotide analog probe and a DNA/RNA sequence by hydrogen bonds in accordance with the rules of Watson-Crick DNA complementarity, Hoogsteen binding, or other sequence-specific binding known in the art. In this context, it is understood in the art that a nucleotide sequence of an oligonucleotide analog described herein need not be 100% complementary to a target nucleic acid sequence to be specifically or selectively hybridizable. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, or 100% complementarity, respectively, not to mention a few. Therefore, in some embodiments, the oligonucleotide analog used herein can be 100% complementary to a target nucleic acid molecule (i.e., a perfect match). In other embodiments, the oligonucleotide analog probe can be at least about 95% complementary, at least about 85% complementary, at least about 70% complementary, at least about 65% complementary, at least about 55% complementary, at least about 45% complementary, or at least about 30% complementary to the target nucleic acid molecule, provided that it can specifically recognizes the amplicons of the converted methylated nucleic acid molecule over those of the converted unmethylated molecule.

The length of the oligonucleotide analog probe described herein can comprise about 5 monomelic units to about 40 monomelic units; about 10 monomelic units to about 35 monomelic units; or about 15 monomelic units to about 35 monomelic units. The term "monomeric unit" of an oligonucleotide analog probe as used herein refers to one nucleotide unit of the oligonucleotide analog.

In certain embodiments, the oligonucleotide analog probe is covalently coupled to the nanoparticle via a functional group. The functional group is typically included in the spacer portion of the oligonucleotide analog probe for covalently binding to the nanoparticle. In some embodiments, the functional group can include a thiol (SH) group, which can for example be used to covalently attach to the surface of the nanoparticle. However, other functional groups can also be used. Oligonucleotides functionalized with thiols at their 3'-end or 5'-end can readily attach to gold nanoparticles. See for example, Mucic et al. Chem. Commun. 555-557 (1996) which describes a method of attaching 3' thiol DNA to flat gold surfaces. The thiol moiety also can be used to attach oligonucleotides to other metal, semiconductor, and magnetic colloids and to the other types of nanoparticles described herein. Other functional groups for attaching oligonucleotides to solid surfaces include phosphorothioate groups (see, for example, U.S. Pat. No. 5,472,881 for the binding of oligonucleotide-phosphorothioates to gold surfaces), substituted alkylsiloxanes (see, for example Grabar et al., Anal. Ghent., 67, 735-743). Oligonucleotides having a 5' thionucleoside or a 3' thionucleoside may also be used for attaching oligonucleotides to solid surfaces. Other functional groups known to the skilled person that can be used to attach the oligonucleotide analog probe to nanoparticles can include but are not limited to disulfides such as disulfide amides; carboxylic acids; aromatic ring compounds; sulfolanes; sulfoxides; silanes, not to mention a few.

A more detailed description of the plasmonic nanoparticles and nanoprobes for the practice of the present method may be found in PCT international patent publication No. WO 2011/087456 A1, which is hereby incorporated by reference in its entirety, with the probe sequences adapted for the target of interest.

As set forth above, this method employs methylation-specific PCR for the specific amplification of at least part of the converted methylated nucleic acid molecule comprising a target region the methylation status of which is to be analyzed, and plasmonic nanoprobe-based colorimetric detection of the resultant amplicons, and thus can be used to determine the methylation status of the target nucleic acid molecule.

The plasmonic nanoprobes developed by the inventors of the present inventioin are highly specific in recognition of nucleic acid sequences. In preferred embodiments, plasmonic gold nanoparticles are functionalized with non-ionic morpholino oligonucleotides. Unlike the DNA-modified gold nanoparticles that are stably dispersed in salt solution, the non-ionic nature of the morpholino oligonucleotides makes the morpholino oligonucleotides-modified nanoparticles much less stable, and only dispersible in solutions with low ionic strength (e.g., [NaCl]<10 mmol/L). An increase of solution ionic strength would lead to solution color change from red to light grey/colorless due to nanoparticle aggregation. However, upon hybridization with negatively charged DNA molecules, the nanoprobes become much more stable due to the increase in surface charge, and the solution remains red at a high ionic strength (e.g., [NaCl] ~100 mmol/L). When temperature rises, sharp melting transition occurs at melting temperature ($T_m$), whereby DNA molecules are released from the nanoprobes, resulting in rapid color change in solution. The nanoprobes are highly specific in recognizing DNA targets, and a single-base mismatch may lead to the decrease in $T_m$ by 5-12° C. This technology allows for accurate end-point detection with standard equipment and a simple workflow. The colorimetric signals can be easily visualized and recorded.

In certain embodiments, the method disclosed herein comprises using a nucleic acid molecule comprising the unmethylated target nucleotide sequence as a negative control, and/or using a nucleic acid molecule comprising the methylated target nucleotide sequence as a positive control.

The present method can be used to determine the methylation status of the human Septin 9 (SEPT9) gene promoter, preferably in the cell-free DNA (cfDNA) fragments circulating in the blood released from colorectal cancer cells. In preferred embodiments, the methylation-specific primers for use in the method have the nucleic acid sequences 5'-ATTAGTTATTATGTCGGATTTCGC-3' (SEQ ID NO: 1) and 5'-CAACACGTCCGCGACCG-3' (SEQ ID NO: 2), the blocker has the nucleic acid sequence 5'-GTTATTATGTTG-GATTTTGTGGTTAATGTGTAG-3' and is labelled with C3 spacer at the 3' end (SEQ ID NO: 3), and the oligonucleotide analog probe used is a morpholino oligonucleotide having the nucleic acid sequence 5'-CAACTACGCGTTAACCGC-GATTTT-3' (SEQ ID NO: 4).

In another aspect, further disclosed herein is a kit for determining the methylation status of a target nucleic acid molecule in a sample, preferably of one or more CpG islands within said target nucleic acid molecule, wherein the kit comprises a pair of methylation-specific primers and a methylation-specific plasmonic nanoprobe as described above.

In certain embodiments, the kit further comprises a blocker sequence as described above.

In certain embodiments, the kit further comprises bisulfite or a salt thereof.

In certain embodiments, the target nucleic acid molecule is human SEPT9 gene, and the kit comprises a pair of methylation-specific primers having the nucleic acid sequences 5'-ATTAGTTATTATGTCGGATTTCGC-3' (SEQ ID NO: 1) and 5'-CAACACGTCCGCGACCG-3' (SEQ ID NO: 2), and a plasmonic gold nanoparticle functionalized with a morpholino oligonucleotide having the nucleic acid sequence 5'-CAACTACGCGTTAACCGCGATTTTT-3' (SEQ ID NO: 4). In preferred embodiments, the kit further comprises a blocker having the nucleic acid sequence 5'-GT-TATTATGTTGGATTTTGTGGTTAATGTGTAG-3' and is labelled with C3 spacer at the 3' end (SEQ ID NO: 3).

Unless otherwise defined, all technical and scientific terms used herein have the same meaning as commonly understood by one of ordinary skill in the art. In case of conflict, the present document, including definitions, will control.

The present invention is further illustrated by the following examples. However, it should be understood, that the invention is not limited to the exemplified embodiments.

EXAMPLES

Materials and Methods

A. Preparation of the Nanoprobes

The preparation of the nanoprobes used herein is similar to that reported previously (Zu Y, et al. Anal Chem. 2011 Jun. 1; 83(11):4090-4; Zu Y, et al. Small. 2011 Feb. 7; 7(3):306-10). Briefly, the MORs modified with disulfide amide at the 3' terminal (Gene Tools, LLC) were treated with dithiothreitol, and then purified by using an NAP-5 column (GE Healthcare). Gold NPs (40 nm-diameter, ~0.1 nM) were mixed with ~2 μM of thiolated MORs and 10 mM of phosphate buffer (pH 7.5), and allowed to incubate at room temperature for 2 h. Next, the MOR-NP conjugates were washed 5 times with a phosphate buffer solution (5 mM, pH 7.5) by centrifugation to remove the unreacted MORs. The conjugates could be used immediately as nanoprobes or stored in 4° C. refrigerator until use. The nanoprobes were stable for at least 6 months when stored at 4° C. Before use, the nanoprobe solutions needed to be uniformly dispersed by vortexing.

B. $T_m$ Measurements

The synthetic targets or PCR amplicons were simply mixed with the specific nanoprobes. Next, the $T_m$ values of the target-probe hybrids were measured with the thermal cycler. The temperature was increased from 30° C. at an interval of 1.0° C. At each temperature, the solution was allowed to incubate for 1 min prior to the color visualization or recording with a camera. When a clear color change from red to light grey was observed, the temperature was recorded as $T_m$.

C. Standard gDNA Samples

Methylated and unmethylated gDNA samples purchased from Promega were used as the standard gDNA template to evaluate the assay performance.

D. Cell Line gDNA Extraction

Extraction of gDNA from cultured cells was performed with the use of the Wizard® SV Genomic DNA Purification System (Promega), according to the manufacturer's instructions. Quantity (ng/μL) and quality (A260/A280 ratio) of the gDNA samples were checked by measuring the absorbance using Nanodrop 1000 (Thermo Scientific). For SW480, RKO and LS174T gDNA samples, the A260/A280 ratios were 1.77, 1.82 and 1.81, respectively.

E. Bisulfite Conversion

Prior PCR amplification, gDNA samples were treated with bisulfite to convert unmethylated cytosine to thymine. The conversion was performed by using the MethylEdge Bisulfite Conversion System (Promega), according to the manufacturer's instructions.

F. aPCR aPCR was used to produce single-stranded DNA targets. PCR solution with a final volume of 25 μL contained gDNA, 12.5 μL of master mix (Fermentas or Promega, 2×), 1000 nM of the forward primer, 100 nM of the reverse primer, and 1000 nM of the blocker. PCR cycling (Table 3) was performed on the PTC-200 DNA Engine (Bio-Rad). The success of the PCR in producing specifically sized amplicons was verified by running a 5-μL aliquot of the PCR products on a 1.5% agarose gel stained with SafeView™ dye.

G. Determination of DNA Methylation

PCR products were mixed with the methylation-specific nanoprobes. The solutions were allowed to incubate at 45° C. for 10 min. The solution color was then recorded by a digital camera. Positive samples were identified by pink solutions, while negative samples were identified by light grey/colorless solutions.

TABLE 1

Sequences of primers, blocker and morpholino probe used in this work.

| SEQ ID NO: | Oligo | Sequence (5' to 3') |
|---|---|---|
| 1 | PCR forward primer | ATT AGT TAT TAT GTC GGA TTT CGC |
| 2 | PCR reverse primer | CAA CAC GTC CGC GAC CG |
| 3 | Blocker sequence | GTT ATT ATG TTG GAT TTT GTG GTT AAT GTG TAG-C3 |
| 4 | Morpholino probe | CAA CTA CGC GTT AAC CGC GAT TTT T |

TABLE 2

Sequences of the synthetic DNA (representing the target regions of methylated and unmethylated SEPT9 genes after bisulfite conversion) used in this work.

| SEQ ID NO: | Oligo | Sequence (5' to 3') |
|---|---|---|
| 5 | Synthetic methylated DNA target | GTT ATT ATG TCG GAT TTC GCG GTT AAC GCG TAG TTG GAT GGG ATT ATT TCG GAT TTC GAA GGT GGG TGT TGG GTT GGT TGT TGC GGT CGC GGA CGT GT |
| 6 | Synthetic unmethylated DNA target | GTT ATT ATG TTG GAT TTT GTG GTT AAT GTG TAG TTG GAT GGG ATT ATT TTG GAT TTT GAA GGT GGG TGT TGG GTT GGT TGT TGT GGT TGT GGA TGT GT |

TABLE 3

Thermal cycler protocol for PCR amplification.

| Initial denaturing | 95° C. | 3 min |
|---|---|---|
| 70-cycle amplification | 95° C. | 20 sec |
| | 62° C. | 30 sec |
| | 72° C. | 20 sec |
| End | 4° C. | Hold |

H. Method

Figure 1:
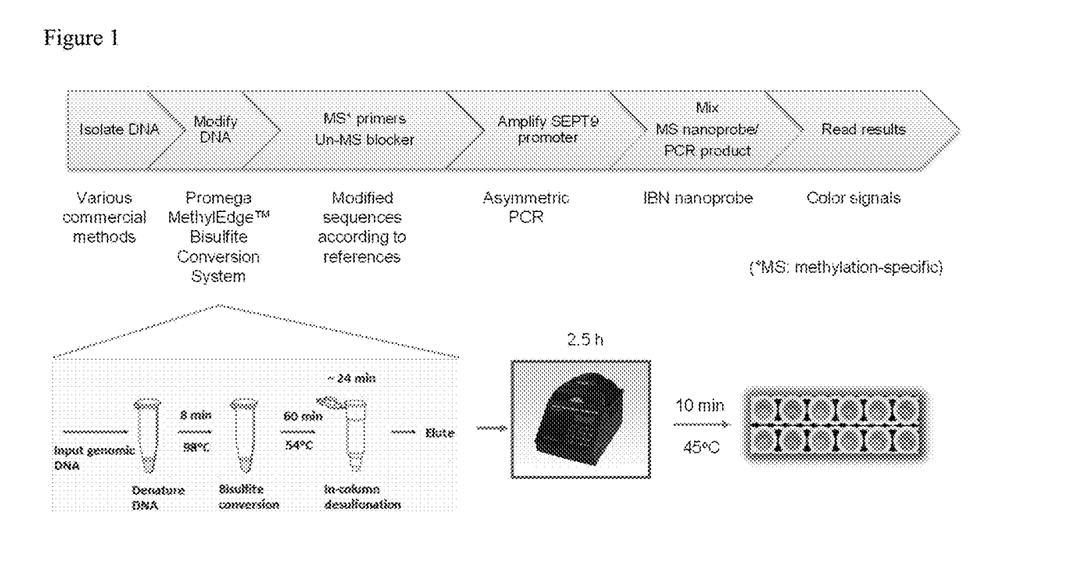
FIG. 1 shows the workflow of the methylation assay described herein.

FIG. 1 shows the workflow of the test. Commercial kits were used to obtain DNA and to perform bisulfite conversion, following which, methylation-specific asymmetric PCR (aPCR) was conducted using a standard thermal cycler. Next, PCR products were mixed with nanoprobe assay solutions, and allowed to incubate at 45° C. for 10 min. Lastly, assay solution color was recorded by a digital camera. Positive samples would display a pink color, while negative samples would turn colorless.

As the concentration of circulating cfDNA in blood is very low, and DNA damage may occur in the bisulfite conversion process, the detection method must be highly sensitive. To increase amplification yield, PCR cycle number was set at 70 cycles.

Figure 2:
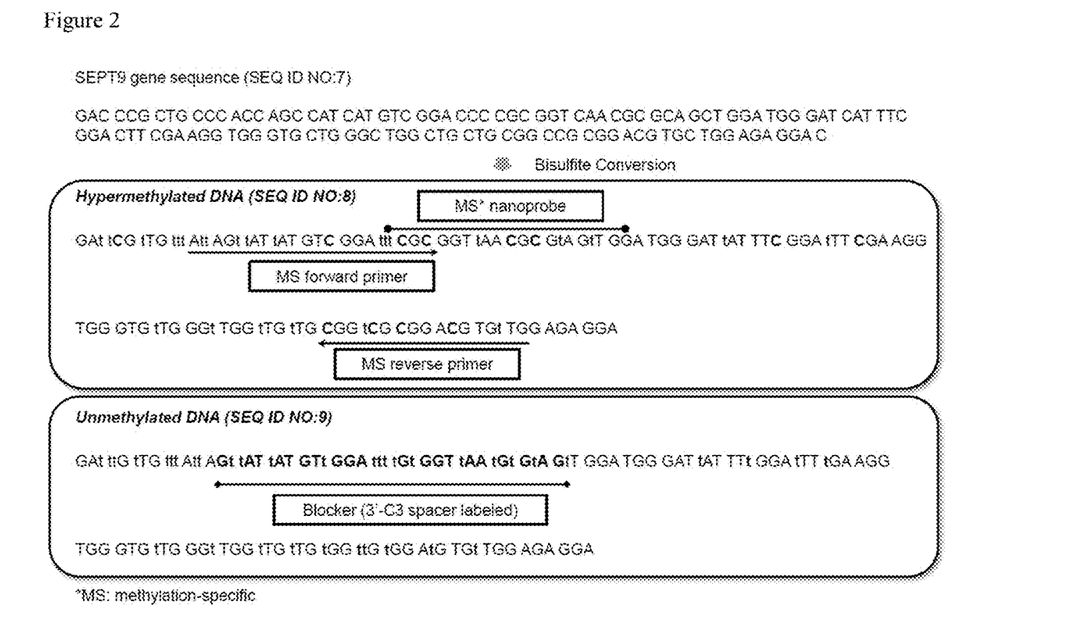
FIG. 2 shows the SEPT9 gene target region and the design of primers, blocker and probe.

In the detection of methylated cfDNA, the interference of normal non-methylated DNA in blood is usually significant. In addition, bisulfite treatment could greatly reduce the level of complexity in the DNA sequences, making the specific detection more difficult. In the protocol, methylation-specific PCR primers that involve at least 3 CpG sites were used. To inhibit the amplification of unmethylated sequences, a blocker sequence was also employed. The PCR products were gauged by a methylation-specific nanoprobe that involves 4 CpG sites. The sequences of PCR primers, blocker, and probe are shown in FIG. 2 and Table 1.

Example 1: Nanoprobe Evaluation

Figure 3:
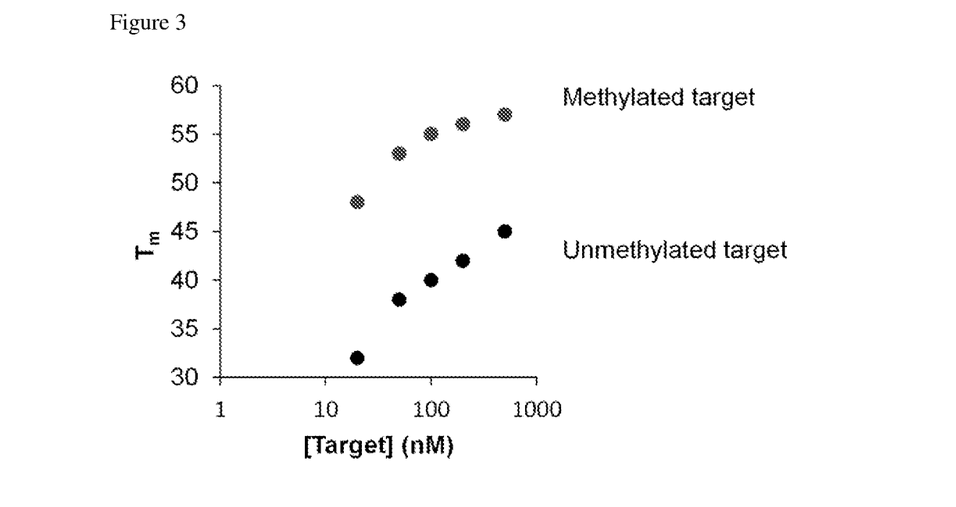
FIG. 3 shows the melting temperature as a function of target concentration for methylated and unmethylated synthetic DNA samples. Error of $T_m$ measurement: ±1° C.

To characterize the nanoprobes, $T_m$ data were measured in the presence of synthetic DNA samples over a broad concentration range of 20 nM to 500 nM (FIG. 3). The synthetic DNA sequences represent the target regions of methylated and unmethylated SEPT9 genes after bisulfite conversion (Table 2). At room temperature (~25° C.), the nanoprobes were stabilized by ≥20 nM of the DNA samples. With the increase in DNA target concentration, $T_m$ increases. The reduction of $T_m$ induced by 4 G/T mismatches between the unmethylated target and the probe was ~15° C.; this allowed for highly specific detection of the methylated target.

Example 2: Assay Performance Evaluation

Figure 4:
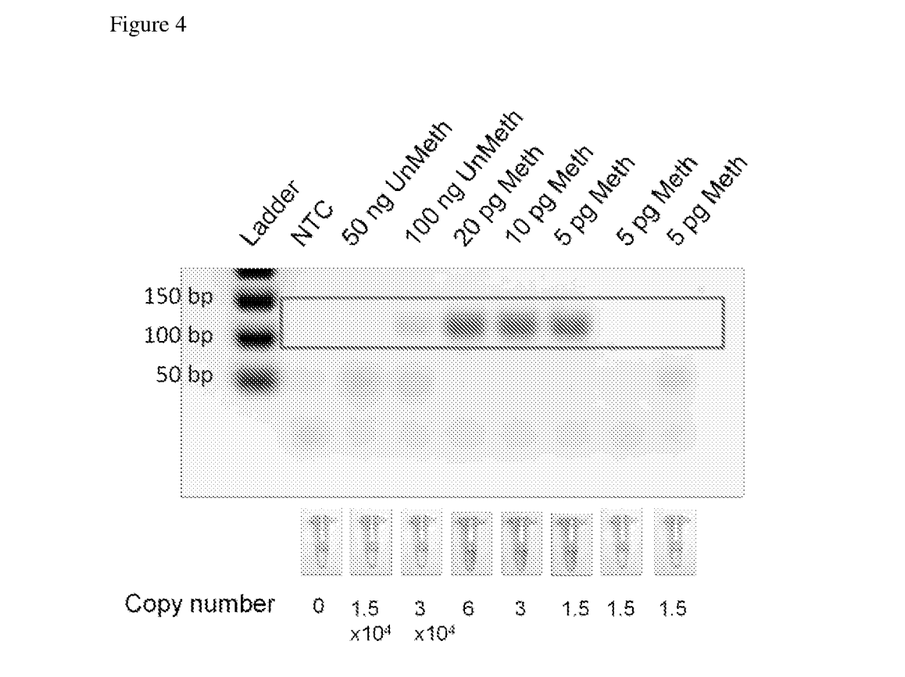
FIG. 4 shows the assay responses towards unmethylated and methylated gDNA samples.

The sensitivity and specificity of the assay were tested by using methylated and unmethylated human genomic DNA (gDNA) samples with concentrations of 5 pM to 100 nM (corresponding copy numbers are 1.5 and $3 \times 10^4$, respectively). FIG. 4 shows that the aPCR produced amplicons consistently for methylated gDNA down to 3 copies. Accordingly, the nanoprobe assay generated positive results. For the samples with even lower concentrations, random positive results were obtained.

Unmethylated gDNA was the interfering background of the assay. The aPCR did not produce specific amplicons for the unmethylated gDNA with concentration up to 50 nM. However, for unmethylated gDNA of 100 nM, amplicon band appeared in the gel electrophoresis analysis, indicating the non-specific amplification of the unmethylated sequences. In this case, the specificity of the methylation-specific primers and the effect of blockers were unable to prohibit the aPCR from generating detectable amount of unmethylated amplicons. Interestingly, in spite of the presence of the non-specific products, the nanoprobe-based assay gave negative results for the samples. The highly specific nanoprobes successfully differentiated the unmethylated sequences from the methylated ones.

Figure 5:
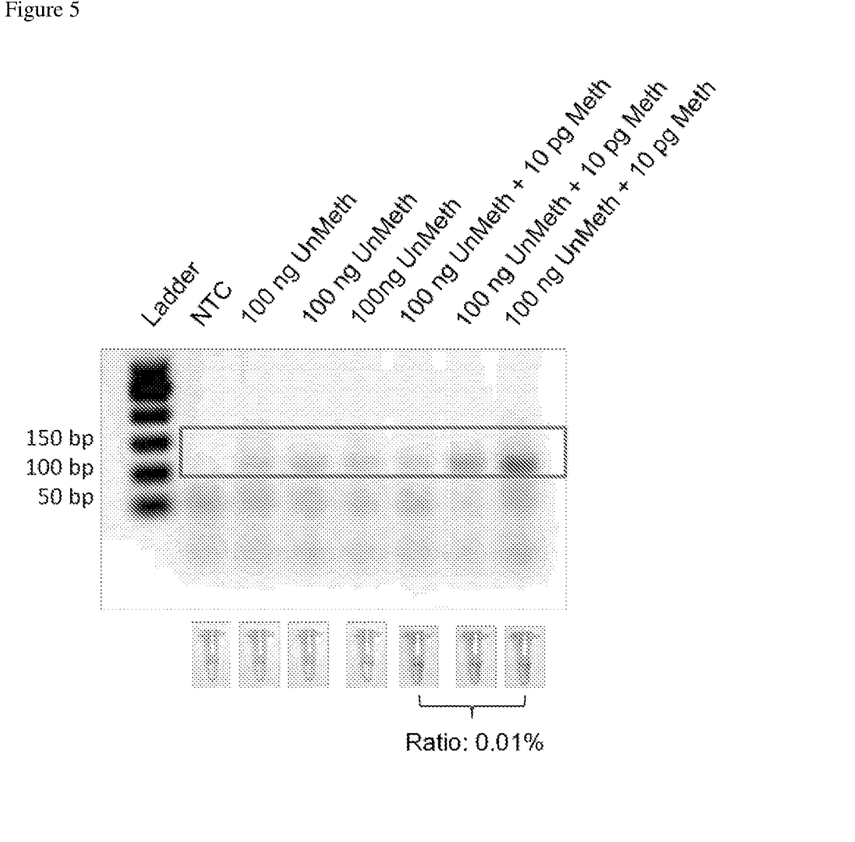
FIG. 5 shows the detection of 0.01% of methylated gDNA in the unmethylated gDNA background.

In another test, the assay sensitivity in the presence of 100 nM of unmethylated gDNA was examined (FIG. 5). Similar to the cases in the absence of unmethylated gDNA, the assay could detect 3 copies of methylated gDNA. Therefore, the assay is able to consistently detect 0.01% of methylated gDNA in the background of unmethylated sequences.

Figure 6:
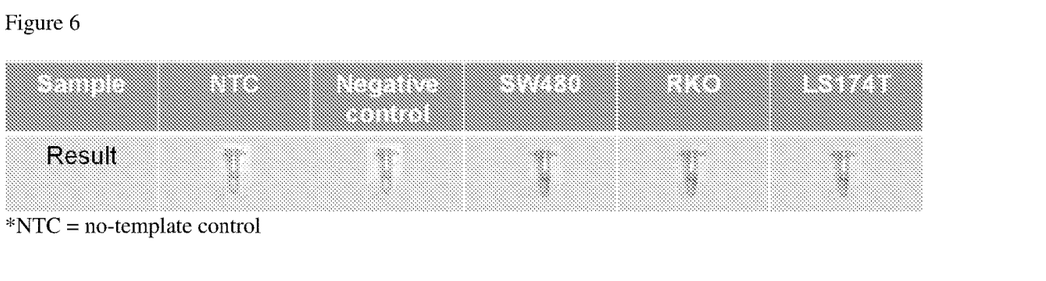
FIG. 6 shows the results of the assays for colorectal cell line samples. The template in the negative control was unmethylated gDNA (~100 ng).

Example 3: Analysis of Cell Line Samples gDNA extracted from several colorectal cancer cell line samples, such as SW480, RKO and LS174T, was also tested. As reported in the literature, these cell lines are all hypermethylated in the promoter region of the SETP9 gene. The assay showed positive results in the methylation analysis for all the samples (FIG. 6).

A highly sensitive and specific assay for SEPT9 gene promoter methylation has been developed. The assay is able to detect 0.01% methylated DNA in the background of unmethylated sequences (i.e. ~3 copies of methylated DNA in 100 nM of unmethylated sequences). This assay would be suitable for methylation analysis of cfDNA in blood samples.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A kit for determining the methylation status of a target nucleic acid molecule in a sample, preferably of one or more CpG islands within said target nucleic acid molecule, wherein the kit comprises a pair of methylation-specific primers and a methylation-specific plasmonic nanoprobe for use in a method of determining the methylation status of a target nucleic acid molecule in a sample, wherein the method comprises the steps of:

(a) bisulfite treatment of the sample for converting the unmethylated cytosine bases in the target nucleic acid molecule to uracil;

(b) amplifying at least part of the converted target nucleic acid molecule, said part comprising a target region the methylation status of which is to be analyzed, in a polymerase chain reaction (PCR), using a pair of methylation-specific primers under conditions allowing such amplification to generate PCR amplification products (amplicons);

(c) contacting the amplicons with a methylation-specific plasmonic nanoprobe comprising a plasmonic nanoparticle and a non-ionic oligonucleotide analog probe covalently coupled thereto, the oligonucleotide analog probe comprising a base sequence that is complementary to the target region, under conditions that allow the oligonucleotide analog probe and the amplicons comprising the target region to hybridize to each other, wherein the probe generates a detectable signal if hybridized to the target nucleic acid molecule that is distinguishable from the signal of the unhybridized probe;

(d) determining the methylation status of the target nucleic acid molecule based on the determination of the melting temperature $T_m$ of the hybrid of the nanoprobe and the target nucleic acid.

2. The kit according to claim 1, wherein the kit further comprises a blocker sequence for use in a method of determining the methylation status of a target nucleic acid molecule in a sample, wherein the method comprises the steps of:

(a) bisulfite treatment of the sample for converting the unmethylated cytosine bases in the target nucleic acid molecule to uracil;

(b) amplifying at least part of the converted target nucleic acid molecule, said part comprising a target region the methylation status of which is to be analyzed, in a polymerase chain reaction (PCR), using a pair of methylation-specific primers under conditions allowing such amplification to generate PCR amplification products (amplicons);

(c) contacting the amplicons with a methylation-specific plasmonic nanoprobe comprising a plasmonic nanoparticle and a non-ionic oligonucleotide analog probe covalently coupled thereto, the oligonucleotide analog probe comprising a base sequence that is complementary to the target region, under conditions that allow the oligonucleotide analog probe and the amplicons comprising the target region to hybridize to each other, wherein the probe generates a detectable signal if hybridized to the target nucleic acid molecule that is distinguishable from the signal of the unhybridized probe;

(d) determining the methylation status of the target nucleic acid molecule based on the determination of the melting temperature $T_m$ of the hybrid of the nanoprobe and the target nucleic acid.

3. The kit according to claim 1, wherein the kit further comprises bisulfite or a salt thereof.

4. The kit according to claim 1, wherein the target nucleic acid molecule is the human SEPT9 gene promoter, and the kit comprises a pair of methylation-specific primers having the nucleic acid sequences 5'-ATTAGTTATTATGTCGGATTTCGC-3' (SEQ ID NO: 1) and 5'-CAACACGTCCGCGACCG-3' (SEQ ID NO: 2), and a plasmonic gold nanoparticle functionalized with a morpholino oligonucleotide having the nucleic acid sequence 5'-CAACTACGCGTTAACCGCGATTTTT-3' (SEQ ID NO: 4).

5. The kit according to claim 4, wherein the kit further comprises a blocker having the nucleic acid sequence 5'-GTTATTATGTTGGATTTTGTGGTTAATGTGTAG-3' and is labelled with C3 spacer at the 3' end (SEQ ID NO: 3).

* * * * *

SEQUENCE LISTING

<160> NUMBER OF SEQ ID NOS: 9

<210> SEQ ID NO 1
<211> LENGTH: 24
<212> TYPE: DNA
<213> ORGANISM: Artificial
<220> FEATURE:
<223> OTHER INFORMATION: synthetic construct

<400> SEQUENCE: 1
attagttatt atgtcggatt tcgc                                          24

<210> SEQ ID NO 2
<211> LENGTH: 17
<212> TYPE: DNA
<213> ORGANISM: Artificial
<220> FEATURE:
<223> OTHER INFORMATION: synthetic construct

<400> SEQUENCE: 2
caacacgtcc gcgaccg                                                  17

<210> SEQ ID NO 3
<211> LENGTH: 33
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (33)..(33)
<223> OTHER INFORMATION: n is G labelled with C3 spacer

<400> SEQUENCE: 3
gttattatgt tggattttgt ggttaatgtg tan                                33

<210> SEQ ID NO 4
<211> LENGTH: 25
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(25)
<223> OTHER INFORMATION: morpholino oligonucleotides

<400> SEQUENCE: 4
caactacgcg ttaaccgcga ttttt                                         25

<210> SEQ ID NO 5
<211> LENGTH: 98
<212> TYPE: DNA
<213> ORGANISM: Artificial
<220> FEATURE:
<223> OTHER INFORMATION: synthetic construct

<400> SEQUENCE: 5

```
gttattatgt cggatttcgc ggttaacgcg tagttggatg ggattatttc ggatttcgaa      60
ggtgggtgtt gggttggttg ttgcggtcgc ggacgtgt                              98

<210> SEQ ID NO 6
<211> LENGTH: 98
<212> TYPE: DNA
<213> ORGANISM: Artificial
<220> FEATURE:
<223> OTHER INFORMATION: synthetic construct

<400> SEQUENCE: 6
gttattatgt tggattttgt ggttaatgtg tagttggatg ggattatttt ggattttgaa      60
ggtgggtgtt gggttggttg ttgtggttgt ggatgtgt                              98

<210> SEQ ID NO 7
<211> LENGTH: 124
<212> TYPE: DNA
<213> ORGANISM: Artificial
<220> FEATURE:
<223> OTHER INFORMATION: Sept9 gene fragment

<400> SEQUENCE: 7
gacccgctgc ccaccagcca tcatgtcgga ccccgcggtc aacgcgcagc tggatgggat      60
catttcggac ttcgaaggtg ggtgctgggc tggctgctgc ggccgcggac gtgctggaga     120
ggac                                                                  124

<210> SEQ ID NO 8
<211> LENGTH: 123
<212> TYPE: DNA
<213> ORGANISM: Artificial
<220> FEATURE:
<223> OTHER INFORMATION: bisulfite treated hypermethylated Sept9 gene
      fragment

<400> SEQUENCE: 8
gattcgttgt ttattagtta ttatgtcgga tttcgcggtt aacgcgtagt tggatgggat      60
tatttcggat ttcgaaggtg ggtgttgggt tggttgttgc ggtcgcggac gtgttggaga     120
gga                                                                   123

<210> SEQ ID NO 9
<211> LENGTH: 123
<212> TYPE: DNA
<213> ORGANISM: Artificial
<220> FEATURE:
<223> OTHER INFORMATION: bisulfite treated unmethylated Sept9 gene
      fragment

<400> SEQUENCE: 9
gatttgttgt ttattagtta ttatgttgga ttttgtggtt aatgtgtagt tggatgggat      60
tattttggat tttgaaggtg ggtgttgggt tggttgttgt ggttgtggat gtgttggaga     120
gga                                                                   123
```